United States Patent
Radowicz et al.

[11] Patent Number: 6,033,503
[45] Date of Patent: Mar. 7, 2000

[54] ADHESIVE SENSING ASSEMBLY FOR END JOINTED BEAM

[75] Inventors: Richard D. Radowicz, Carmel, Calif.; Steven K. Radowicz, 471 Los Laureles, Carmel Valley, Calif. 93924

[73] Assignee: Steven K. Radowicz, Carmel Valley, Calif.

[21] Appl. No.: 09/272,817

[22] Filed: Mar. 19, 1999

Related U.S. Application Data

[63] Continuation-in-part of application No. 08/841,892, May 5, 1997, abandoned.

[51] Int. Cl.[7] .............................. B32B 31/00; B32B 33/00
[52] U.S. Cl. ..................... 156/64; 73/104; 73/150 R; 118/691; 118/712; 156/350; 156/356; 156/378; 156/379; 250/453.11; 250/458.1; 250/559.03; 250/559.42; 250/559.45; 250/559.47; 403/364; 427/8; 427/9; 427/10
[58] Field of Search ........................ 73/150 R, 104; 250/453.11, 458.1, 559.03, 559.42, 559.45, 559.47; 403/364; 156/64, 350, 378, 379, 356; 118/691, 712; 427/8–10

[56] References Cited

U.S. PATENT DOCUMENTS

| | | | |
|---|---|---|---|
| 3,938,467 | 2/1976 | Radowicz | 118/2 |
| 4,220,114 | 9/1980 | Radowicz | 118/411 |
| 4,356,045 | 10/1982 | Elford et al. | 156/64 |
| 4,914,964 | 4/1990 | Speiser | 73/865.9 |
| 4,918,321 | 4/1990 | Klenk et al. | 250/559.45 |
| 4,984,172 | 1/1991 | Luminari | 250/559.42 |

*Primary Examiner*—Deborah Jones
*Assistant Examiner*—Robert R. Koehler
*Attorney, Agent, or Firm*—Beyer & Weaver, LLP

[57] ABSTRACT

Methods and apparatus for detecting imperfections in adhesive coatings formed on fingers of beams are disclosed. The present invention relates, in one aspect, to a method for preparing a first work piece for joining with a second work piece. The method involves forming a finger in the first work piece, then applying an adhesive coating on the finger. A determination is made to determine whether the adhesive coating is defective through the used of a sensing mechanism which is arranged to scan across a portion of the finger. In one embodiment, a defect in the adhesive coating on the finger is defined as a void.

20 Claims, 7 Drawing Sheets

ADHESIVE SENSING ASSEMBLY FOR END JOINTED BEAM

CROSS REFERENCE TO RELATED APPLICATION

The present U.S. Patent Application is a continuation-in-part of U.S. patent application Ser. No. 08/841,892, filed May 5, 1997, now abandoned, which is incorporated herein by reference in its entirety.

BACKGROUND OF THE INVENTION

1. Field of Invention

The present invention relates generally to methods and apparatus for use in monitoring the application of adhesive to finger joints and other wood surfaces, such as edge-glued surfaces and I-beams.

2. Background

In industries which use wood, e.g., the construction industry and the furniture-making industry, the practice of joining smaller pieces of wood together to create larger pieces of wood has long been employed. Smaller pieces of wood may be joined or bonded together to form a large piece of wood which may then be used for any suitable purpose, as for example, to create a table surface. Alternatively, pieces of wood which would otherwise be difficult to use because they are of a relatively small size may be joined together to form a larger piece of wood.

In order for the smaller pieces, or blocks, of wood to be joined together, the ends of the blocks are often cut to form "fingers," or interlocking structures. Although these fingers may take any suitable form, the fingers are generally formed as pointed extensions on the end of a block of wood that are arranged to interlock with fingers formed on the end of another block of wood. FIG. 1a is a diagrammatic representation of the ends of two beams, or blocks of wood, which may be assembled to form an end jointed beam. In general, end jointed beams are created from "scrap," e.g., small, pieces of lumber which might otherwise be discarded. However, as previously mentioned, end jointed beams may also be created from smaller pieces of lumber simply because a larger piece of lumber is desired.

A first beam 104 includes fingers 108 which are cut into the end of first block 104. It should be appreciated that first block 104 may be a board. A second block 112, like first block 104, includes fingers 116 that are cut into the end of second block 112. As shown, first block 104 includes seven fingers 108, and second block 112 includes seven fingers 116. It should be appreciated, however, that the number of fingers may be widely varied and is, in general, dependent at least in part upon the size of the block. Fingers 108 and fingers 116 are arranged to interlock such that first block 104 and second block 112 may together form a single overall beam, block, or board.

In order for blocks 104 and 112 to be securely fitted together, adhesive is generally applied on fingers 108 and/or fingers 116. It should be appreciated that adhesive may be applied on both the top surfaces 110 of fingers 108 and the bottom surfaces of the fingers. Alternatively, it may be possible for adhesive to be applied on just one surface of fingers, i.e., either top surfaces of fingers or bottom surfaces of fingers. By way of example, adhesive may be applied to top surfaces 110 of fingers 108 such that a bond is formed between fingers 108 and fingers 116 when fingers 108 and fingers 116 are interlocked. FIG. 1b is a diagrammatic representation of first block 104 with an adhesive coating 120 applied on the top surfaces of fingers 108. As shown, adhesive coating 120 substantially covers the top surfaces of fingers 108, i.e., adhesive coating 120 covers the top surfaces of fingers substantially between tips 119 and roots 121.

Adhesive application systems which are used to deposit adhesive on the surfaces of fingers of blocks, e.g., surfaces 110 of fingers 108, generally involve spreading a coating of adhesive on the surfaces. Although any suitable system may be used to deposit adhesive on fingers, two particularly suitable systems are described in U.S. Pat. Nos. 3,938,367 and 4,220,114, which are incorporated herein by reference in their entirety.

In general, adhesive application systems have been shown to be effective in forming coatings of adhesive on surfaces of fingers. However, the coatings of adhesive on surfaces of fingers may be uneven. In other words, there are instances when adhesive is not successfully applied to predefined locations. By way of example, air bubbles in adhesive may create voids in adhesive coatings. Alternatively, when an adhesive application system either malfunctions or exhausts an available supply of adhesive, the coating of adhesive on the surface of a finger may be uneven, or, in some cases, nonexistent.

As shown in FIG. 1c, an adhesive coating 122 on the top surface of a finger 108 of block 104 may include a void 124, or a section which is intended to be covered with adhesive but is left without adhesive. Void 124 may occur for any number of reasons, as for example when air bubbles are present in adhesive when adhesive coating 122 is formed, as mentioned above.

When a surface for a finger which is intended to be covered with adhesive is not properly covered with adhesive, the overall block created when fingers of two or more blocks are interlocked and "glued" together is considered to be imperfect. In other words, the bond between the pieces which make up the overall, or end-jointed, block, however strong the bond may be, is often considered to be marred. Such an end-jointed beam is generally considered to be a imperfect because of a void in the adhesive layer.

It should be appreciated that when smaller beams with fingers that are improperly coated with adhesive are joined together, the resulting end-jointed block may fail a quality inspection process. Typically, the quality inspection process is performed visually. Although visual inspection often works well, it is time consuming, relatively expensive and highly dependent upon the abilities of the inspector. Therefore, what is desired is an efficient method and apparatus for determining whether adhesive coatings are properly formed on the fingers that are to be used in a finger joint.

SUMMARY OF THE INVENTION

The present invention relates, in one aspect, to a method for preparing a work piece for use in forming an overall block such as an end-jointed block. Typically, for a work piece that is to be used in the formation of an end-jointed board, one or more fingers are formed on a work piece, and an adhesive coating is applied to the fingers to facilitate gluing the work piece to another. A sensing mechanism is then used to determine whether the adhesive coating on the fingers contains an imperfection. In some embodiments, the sensing mechanism is arranged to use principles of luminescence to determine the luminescence on the finger of the work piece. The strengths of the luminescences associated with the finger, or the magnitude of the luminescence signals associated with the finger, are then used to determine whether the adhesive coating on the finger of the work piece contains an imperfection.

In one embodiment, when it is determined that the adhesive coating on the fingers is imperfect, the work piece is marked to indicate that the work piece includes an imperfection. The work pieces may be marked in a variety of manners, as for example by direct marking with a dye or the like, indirect marking by emitting a warning signal such as a strobe light or sound, or by noting the imperfection in a database. In another embodiment, the work pieces with imperfections may be physically removed from a production line.

These and other advantages of the present invention will become apparent upon reading the following detailed description and studying the various figures of the drawings

BRIEF DESCRIPTION OF THE DRAWINGS

The invention may best be understood by reference to the following description taken in conjunction with the accompanying drawings in which.

DETAILED DESCRIPTION OF THE EMBODIMENTS

A presently preferred method and apparatus for detecting imperfections in adhesive coatings formed on fingers of beams in accordance with the present invention will be described below making reference to the accompanying drawings. As the detection of imperfections on fingers of boards which are to be assembled into end-jointed beams or boards is typically performed by a human, the process of detecting imperfections is often both inconsistent and difficult to control. To this end, the ability to consistently detect imperfections on fingers, or other types of joint mechanisms, of beams would improve the quality control process associated with the fabrication of end-jointed beams and/or boards.

One method for detecting imperfections, e.g., voids, in adhesive coatings formed on the surfaces of fingers of a component block, or a finger-jointed board, involves scanning at least a portion of the surface of a finger using sensors. The sensors, which may operate using principles of reflectivity, are oriented to scan at least part of the top surfaces of fingers to thereby identify differences between bare areas of the surfaces and areas of the surfaces which are covered with adhesive. The same approach is an effective method for identifying imperfections in coatings of laminating material on a block as well.

A second method for detecting imperfections in adhesive coatings formed on surfaces such as surfaces of the fingers of finger jointed blocks, surfaces of I-joist beams, and surfaces of edge glued panels, involves scanning the surfaces using luminescence sensors. The luminescence or, more specifically, luminescence signals associated with a surface vary depending upon imperfections in the coating on the surface. Specifically, luminescence signals decrease as the ratio void areas, or other areas of imperfections, to adequately coated areas increases.

Detecting voids in adhesive coatings on the surfaces of fingers of a component beam typically occurs prior to the assembly of an overall end-jointed board. By detecting voids on surfaces prior to the final assembly of an end-jointed board, the voids may be readily eliminated by, for example, re-coating the surfaces with adhesive. As such, the process of inspecting blocks to determine if the surfaces of the fingers of the blocks are properly covered with adhesive may typically be incorporated as a part of an overall end-jointed board assembly process.

Figure 1A:
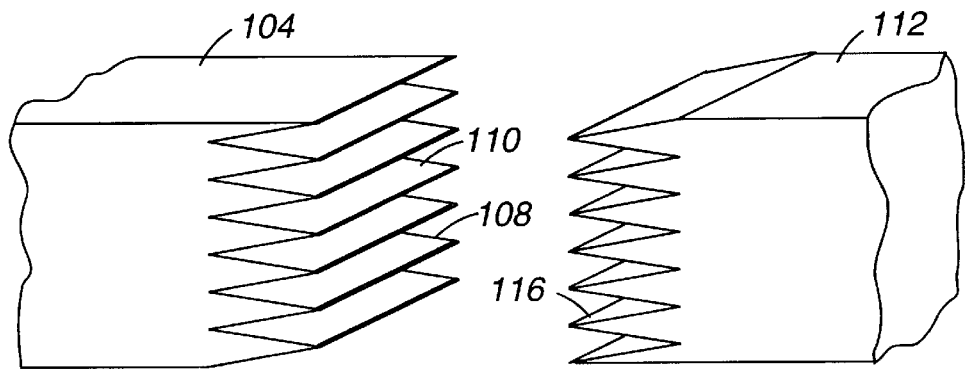
FIG. 1a is a diagrammatic representation of the ends of two blocks which may be assembled to form an end jointed block.
Figure 1B:
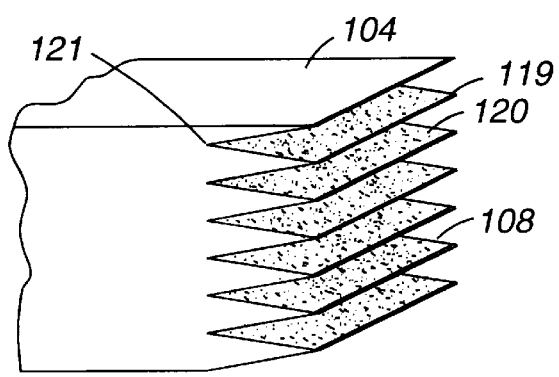
FIG. 1b is a diagrammatic representation of a block with fingers on which an adhesive coating has been applied.
Figure 1C:
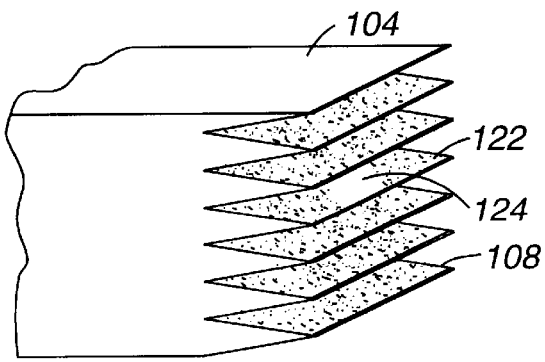
FIG. 1c is a diagrammatic representation of a block with fingers on which an imperfect adhesive coating has been applied.
Figure 2:
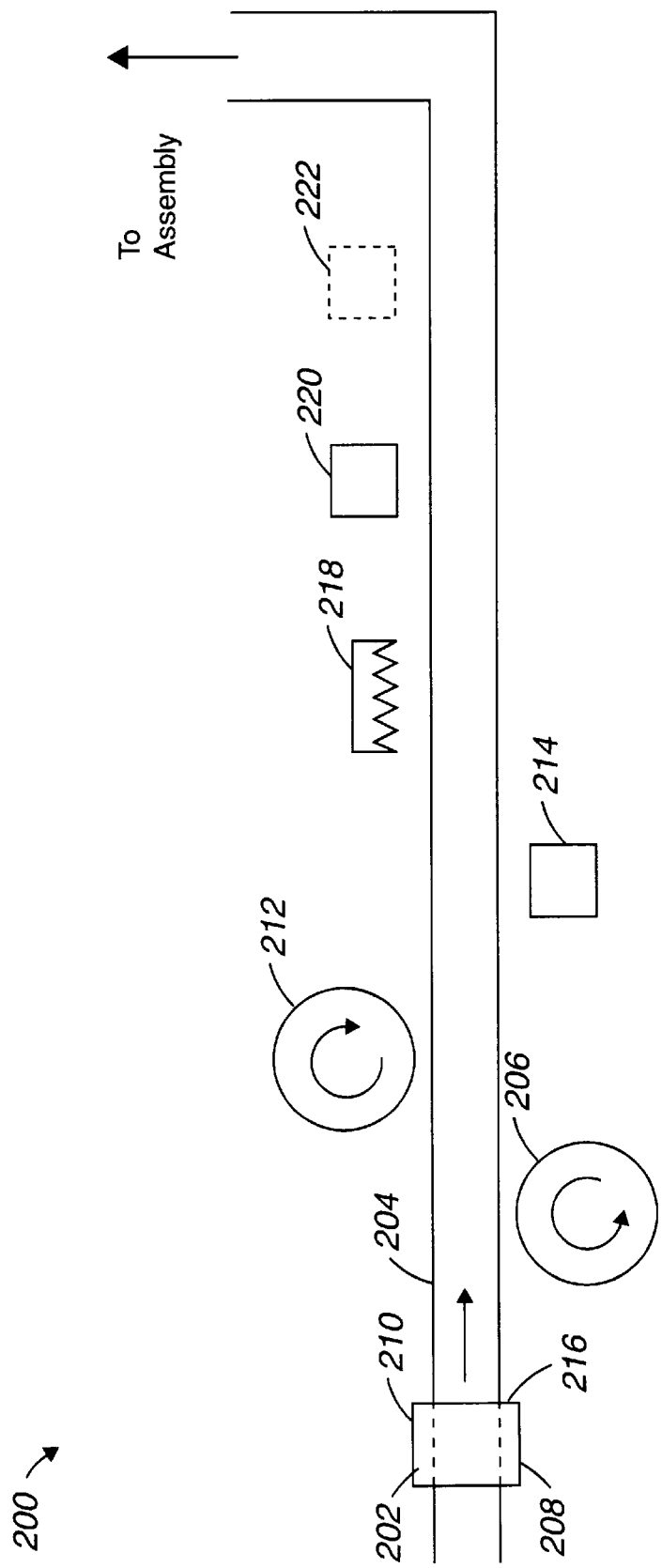
FIG. 2 is a diagrammatic representation of a portion of the fabrication process of an end-jointed beam in accordance with a first embodiment of the present invention.

With reference to FIG. 2, the processes of creating fingers in a work piece, applying adhesive to the fingers, and detecting the adhesive on the fingers will be described in accordance with an embodiment of the present invention. It should be appreciated that the processes may vary depending upon, for instance, the type of adhesive detection that is used. Another example of the processes used to apply and detect adhesive will be described below with reference to FIG. 7.

Along an end-jointed beam assembly line 200, a work piece 202, e.g., a board or a block of wood, is oriented on a conveyer belt 204 which is generally arranged to transport work piece 202 between different processes along end-jointed block assembly line 200. It should be appreciated that work piece 202 may be of any suitable size, and, further, that the material from which work piece 202 is created may be any type of wood or other material which is suitable for use in creating end-jointed boards, or end-jointed composite pieces. In general, the size of conveyer belt 204, as well as the location of process equipment along end-jointed beam assembly line 200, may be altered to accommodate work pieces of various sizes.

A first cutter head 206 is arranged to profile work piece 202 such that fingers (not shown) are formed in a first end 208 of work piece 202. First end 208 may be considered to be a "bonding," e.g., interlocking, surface of work piece 202. In other words, fingers which are cut into work piece 202 at first end 208 are typically arranged to be interlocked with fingers of another work piece. The number of fingers cut into work piece 202 at first end 208 may depend on any number of parameters which include, but are not limited to, the size of work piece 202, the material from which work piece 202 is created, the finger length, and the finger pitch/index which, in turn, may depend upon the intended use of the overall, assembled board. By way of example, the number of fingers in work piece 202 may range from approximately two fingers to approximately sixty fingers. It should be appreciated that first cutter head 206 may generally be any type of cutting mechanism, as for example a circular saw cutting mechanism or stacked knife assembly.

For embodiments in which fingers are desired in both first end 208 and a second end 210 of work piece 202, a second cutter head 212 is arranged to profile fingers in second end 210. That is, if work piece 202 is to be bonded to two other work pieces, then fingers are preferably created in both first end 208 and second end 210 of work piece 202.

In the described embodiment, after fingers are profiled in work piece 202, conveyer belt 204 transports work piece 202 through a sensing path of a leading edge block sensor 214. Leading edge block sensor 214, which can be located on either side of 204, is arranged to sense, when a leading edge 216 of work piece 202 passes leading edge block sensor 214. As the speed at which conveyer belt 204 and work piece 202 are moving is typically known, the application of adhesive to the fingers of work piece 202 may be controlled. That is, the surface area of the fingers that is to be coated with adhesive may be partially determined. By way of example, the time at which leading edge 216 of work piece 202 passes leading edge block sensor 214 may be recorded. Then, an applicator head 218 may begin dispensing adhesive, e.g., glue, after a delay which may determined based upon the speed at which wood piece 202 is moving and the distance between leading edge block sensor 214 and applicator head 218. Finally, the size, e.g., width, of work piece 202 may be used in conjunction with the speed at which work piece 202 is moving to determine when the dispensing of adhesive for work piece 202 should end. Additionally, an encoder may be used in conjunction with block sensor 214 in order to adjust a glue pattern in accordance with speed changes of conveyer belt 204.

Although any suitable applicator head 218, or glue roller, may be used in the application of adhesive to the surfaces of fingers of work piece 202, applicator head 218 is preferably either the applicator head described in above-mentioned U.S. Pat. Nos. 3,938,367 and 4,220,114. It should be appreciated that while the surface area of the fingers that is coated with adhesive may be partially dependent upon the amount of time adhesive is applied to the surfaces of the fingers, the surface area covered with adhesive is also dependent upon the physical size of applicator head 218.

As shown, applicator head 218 is arranged to dispense adhesive only on fingers profiled in second end 210 of work piece 202. In most end-jointed block assembly processes, when an end of a first beam is to be bonded to an end of a second beam, only one of the "bonding pair" of ends is typically coated with adhesive. However, it should be appreciated that for embodiments in which both ends of bonding pairs are to be coated with adhesive, both first end 208 and second end 210 of work piece 202 are then coated with adhesive. Accordingly, an additional applicator head (not shown) may be added to end-jointed beam assembly line 200 to serve the purpose of coating first end 208 of work piece 202 with adhesive.

After adhesive is applied to work piece 202, conveyer belt 204 transports work piece 202 to a detector mechanism 220. Detector mechanism 220, e.g., adhesive detector 220, is generally arranged to sense whether adhesive has been properly applied to the fingers of work piece 202. By way of example, if there is an unexpected void in the adhesive coating on a finger of work piece 202, adhesive detector 220 will detect the void and alert an individual who is monitoring end-jointed beam assembly line 200 that the adhesive coating on work piece 202 is defective. While any suitable adhesive detector may be used to detect anomalies in an adhesive coating, in one embodiment, adhesive detectors which measure the differences in reflectivity of a portion of a surface which is bare and a portion of a surface which is covered with adhesive, may be used. One embodiment of such an adhesive detector will be described in more detail below with reference to FIGS. 3, 4a, and 4b.

As shown, adhesive detector 220 is positioned to detect whether an adhesive coating has been properly applied to the surfaces of fingers profiled in second end 210 of work piece 202. It should be appreciated that for embodiments in which adhesive is also applied to the surfaces of fingers profiled in first end 208 of work piece 202, an additional adhesive detector may be included in end-jointed beam assembly line 200.

Using information from leading edge block sensor 214, adhesive detector 220 may be arranged to be activated only when appropriate. That is, adhesive detector 220 may be calibrated to be aware of when it is appropriate to scan a surface for adhesive. In some embodiments, portions of the surfaces of fingers, as for example the leading and trailing edges of the block, may intentionally be left bare, or uncoated with adhesive. It should be appreciated that if the entire surface of a finger is scanned for a lack of adhesive, areas which are intended to be free of adhesive may be classified as defects. As such, adhesive detector 220 may be calibrated such that adhesive detector 220 only scans the portions of the surfaces of fingers where adhesive coatings are expected.

An optional dye failed unit indicating mechanism 222, as shown, may be located such that work piece 202 passes from adhesive detector 220 to indicating mechanism 222. In one embodiment, indicating mechanism 222 is a dye dispensing mechanism that is arranged to place a dye mark on wood piece 202 in the event that there is a defect in the adhesive coating on work piece 202. Such a dye mark would serve the purpose of indicating to an individual that the marked work piece 202 is considered to be defective. Indicating mechanism 222 is generally coupled to adhesive detector 220, since the operation of indicating mechanism 222 is dependent upon whether a defect has been detected by adhesive detector 220. It should be appreciated that when indicating mechanism 222 is a dye dispensing mechanism, indicating mechanism 222 is calibrated to control the dispensing of dye and, therefore, to prevent accidentally marking the wrong work piece.

Although indicating mechanism 222 is typically a dye dispensing mechanism that physically marks imperfect work pieces, it should be appreciated that indicating mechanism 222 may generally be any suitable "imperfection processor." By way of example, indicating mechanism 222 may be an air kicker that is arranged to "kick" or otherwise remove imperfect work pieces from end-jointed beam assembly line 200. Alternatively, indicating mechanism 222 may be a light that turns on, or a horn that sounds, when an imperfect work piece is identified.

Once defective, or imperfect, work pieces have been "marked" by indicating mechanism 222, the imperfect work pieces may be removed from end-jointed beam assembly line 200. In one embodiment, imperfect work pieces that are marked with dye may be allowed to continue on end-jointed beam assembly line 200, until a predetermined number of imperfect work pieces have been identified. By way of example, imperfect work pieces may be allowed to continue on end-jointed beam assembly line 200 until the total number of imperfect work pieces identified exceeds the predetermined number of imperfect work pieces which are considered to be acceptable. Alternatively, imperfect work pieces may be allowed to continue along end-jointed beam assembly line 200 until a predetermined number of sequentially occurring imperfect work pieces is identified. In general, the predetermined number of imperfect work pieces may be widely varied, as for example in the range of approximately two to approximately ten. Once the predetermined number of imperfect work pieces is reached, action is typically taken to rectify any problems which may result in imperfect work pieces. It should be appreciated that imperfect work pieces may be counted using a counting mechanism that is coupled to adhesive detector 220 such that any time an imperfect work piece is identified, the counter is incremented.

It should be appreciated that in some embodiments, e.g., embodiments in which there is a low tolerance for imperfect work pieces, all imperfect work pieces are removed from end-jointed beam assembly line 200. In such embodiments, a predetermined number of defective work pieces may be used as a measure for determining when end-jointed beam assembly line 200 should be shut down in order to identify and to address the problems on end-jointed beam assembly line 200 which result in defective work pieces. For example, in one embodiment, the presence of three sequentially occurring defective work pieces may signify that end-jointed assembly line 200 should be taken off-line to address the issue of defective work pieces.

In the described embodiment, if work piece 202 is not defective and, therefore, is not marked with dye, conveyer belt 204 moves work piece 202 from the adhesive application and detection portion of end-jointed beam assembly line 200 to a portion of end-jointed beam assembly line 200 that is arranged to assemble work pieces together. Assembling work pieces together generally involves bonding work pieces together to create an end-jointed beam, e.g., interlocking and joining complementary ends of work pieces, usually using a high pressure force, as will be appreciated by those skilled in the art.

Figure 3:
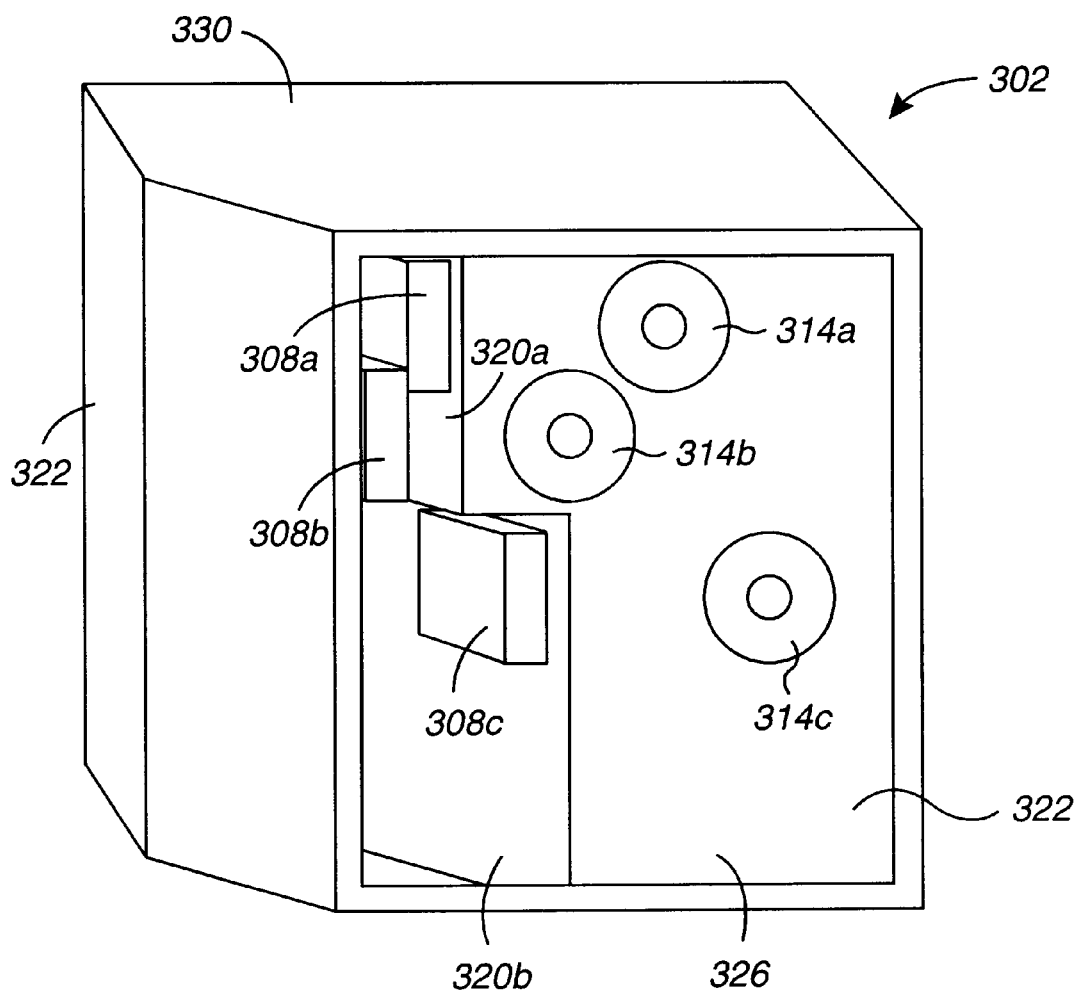
FIG. 3 is a diagrammatic representation of an adhesive detector suitable for use in determining if an adhesive coating has been properly applied to a surface of a finger in accordance with the first embodiment of the present invention.

Referring next to FIG. 3, an adhesive detector suitable for use in determining if an adhesive coating has been properly applied to a surface of a finger will be described in accordance with an embodiment of the present invention. That is, one embodiment of adhesive detector 220 of FIG. 2 will be described. Adhesive detector 302 includes transceivers 308 and transceivers 314, or sensors, which may serve as emitters and receivers. As shown, transceivers 308 are used as emitters, e.g., light emitters, while transceivers 314 are used as receivers, or transducers.

Although any suitable transceivers may be used, in the described embodiment, transceivers 308, referred to herein as emitters 308, are preferably emitters which are capable of transmitting relatively high powered light, which may either be visible light or UV light. Transceivers 314, which will be referred to herein as receivers 314, are preferably receivers which are sensitive to the high powered light that is emitted by emitters 308, e.g., receivers 314 are preferably sensitive enough to concentrate light which originates from emitters 308 into a relatively small area. By way of example, suitable emitters 308 include, but are not limited to, components associated with the FS-T1 emitters which are available commercially from Keyence Incorporated of Osaka, Japan, while suitable receivers 314 include components associated with FS-T2 receivers, which are also available commercially from Keyence Incorporated. It should be appreciated that in the described embodiment, emitters 308 are a part of emitter assemblies that includes light sources which transmit light through fiberoptic cables (not shown), as for example cables FU-12 and FU-7F, available commercially from Keyence Incorporated, to the emitters 308. Likewise, receivers 314 are part of receiver assemblies that are used to analyze the light received by receivers 314.

In the described embodiment, emitters 308 are arranged to transmit light onto the surfaces of the fingers, while receivers 314, or optical detectors, are arranged to receive light reflected off the surfaces of the fingers. As shown, emitters 308a and 308b are mounted on a side surface 320 of sensor mount 322. Side surface 320 is "stepped," i.e., a first portion 320a of side 320 surface is somewhat offset from a second portion 320b of side 320 surface. Emitter 308a is on first portion 320a, as is emitter 308b, while emitter 308c is mounted on second portion 320c. As shown, emitters 308 are all slightly offset with respect to each other.

In general, side surface 320 is sloped. That is, side surface 320 forms an angle with a side wall 322 of detector housing 330. Side surface 320 is sloped such that light emitted from emitters 308 may be efficiently reflected off of the top surfaces of fingers, for example, back to receivers 314, as will be described below with respect to FIGS. 4a and 4b. It should be appreciated that in some embodiments, light may instead reflect off the bottom surfaces of fingers.

Receivers 314 are mounted on a front surface 326 of sensor mount 322. Receivers 314 are located such that each receiver 314 is paired with a corresponding emitter 308. In other words, receiver 314a is placed such that receiver 314a receives light emitted from emitter 308a, after the light has been reflected off of the top surface, or surfaces, of one or more fingers. Similarly, receiver 314b is positioned to eventually receive light emitted from emitter 308b, and receiver 314c is positioned to eventually receive light emitted from emitter 308c.

The number of emitters 308 and receivers 314 is dependent at least in part upon the size of the work piece, or block, that is being scanned. Larger work pieces, or work pieces with many fingers, may require more emitters 308 and receivers 314, while smaller work pieces may require fewer emitters 308 and receivers 314. In the described embodiment, each emitter and receiver pair, e.g., emitter 308a and receiver 314a, is arranged to detect whether the adhesive coatings on the top or bottom surfaces of two adjacent fingers are acceptable. In general, the emitter and receiver pairs may each be arranged to monitor the adhesive coatings on the top surfaces of more than two adjacent fingers. Alternatively, the emitter and receiver pairs may each be configured to monitor the adhesive coating on the top surface of a single finger.

It should be appreciated that front surface 326 is sloped to correspond to the slope of side surface 320. That is, while side surface 320 is sloped to enable emitters 308 to flood light onto the top or bottom surfaces of fingers, i.e., to create a beam pattern, front surface 326 is sloped to enable reflected light to be efficiently received by receivers 314, as will be described below with respect to FIGS. 4a and 4b. Although the slopes of side surface 320 and front surface 326 may be widely varied, in the described embodiment, the slope of side surface 320 is in the range of approximately 15–50 degrees, measured with respect to side wall 322. The corresponding slope of front surface 326, measured with respect to a clear cover plate 340 that is a part of detector housing 330, may be in the range of approximately 0–20 degrees, e.g., approximately 5–10 degrees. By way of example, when side surface 320 has a slope of approximately 35 degrees, front surface may have a corresponding slope of approximately six degrees.

Figure 4A:
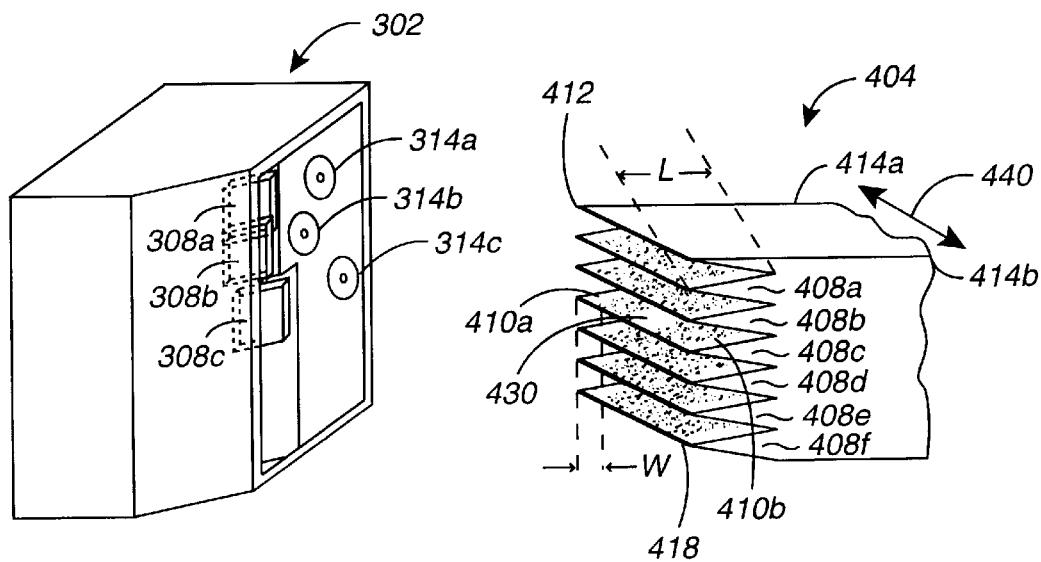
FIGS. 4a is a diagrammatic representation of a finger-jointed beam and an adhesive detector which is suitable for use in scanning the fingers of the beam in accordance with the first embodiment of the present invention.
Figure 4B:
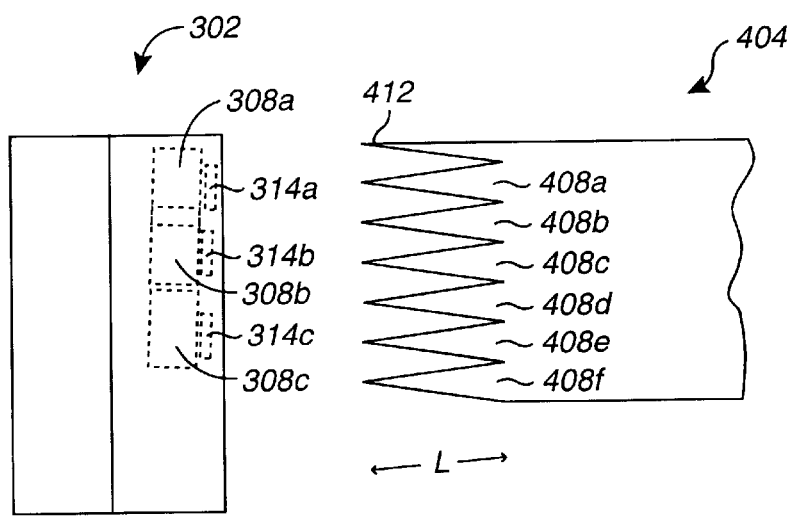
FIG. 4b is a diagrammatic side-view representation of an adhesive detector and a finger-jointed beam aligned in a scanning orientation in accordance with the first embodiment of the present invention.

With reference to FIGS. 4a and 4b, a method of scanning the surfaces of the fingers of a beam using the adhesive detector of FIG. 3 will be described in accordance with an embodiment of the present invention. It should be appreciated that, as shown in FIG. 4a, adhesive detector 302 and a beam 404 are not aligned as adhesive detector 302 and beam 404 would typically be aligned when adhesive detector 302 is situated to scan the surfaces of fingers 408 of beam 404. Rather, adhesive detector 302 and beam 404 are shown at slight angles such that both adhesive detector 302 and surfaces of fingers 408 may readily be viewed for purposes of illustration. FIG. 4b is a diagrammatic side-view representation of adhesive detector 302 and beam 404 as aligned when adhesive detector 302 is situated to scan the surfaces of fingers 408.

Emitter 308a is arranged to illuminate at least a portion of the top surfaces of fingers 408a and 408b. Similarly, emitter 308b is arranged to illuminate at least a portion of the top surfaces of fingers 408c and 408d, while emitter 308c is arranged to illuminate at least a portion of the top surfaces of fingers 408e and 408f. As emitters 308 are scanned across fingers 408 in the direction indicated by arrow 440, different portions of fingers 408 are illuminated. It should be appreciated that, typically, beam 404 is moved, e.g., moved by a conveyer belt, to enable emitters 308 to be scanned across fingers 408 although, alternatively, adhesive detector 302 may be moved instead.

In general, portions of the surfaces of fingers 408 may intentionally be left bare, or free of an adhesive coating. These bare portions, or "spared areas," as for example spared areas 410a and 410b, are typically located at the edges 414 of fingers 408. The width W of spared areas 410 is typically in the range of approximately an eighth of an inch to half of an inch, although it should be appreciated that the width W may be widely varied depending upon the overall size of beam 404 and the adhesive coating. Spared areas 410 are provided at edges 414 of fingers 408 as shown to prevent leakage of adhesive over edges 414 either during application of the adhesive or when fingers 408 are interlocked and bonded with fingers of another beam (not shown).

In general, using feedback from leading edge sensors which were mentioned above with respect to FIG. 2, adhesive detector 302 may be controlled. That is, the operation of adhesive detector 302 may be controlled such that emitters 308 and receivers 314 operate to scan the surfaces of fingers 408 only at desired times. By way of example, the width of beam 404 and the width W of spared areas 410 is generally known. As such, given the time at which the leading edge, e.g., edge 414a, passes a leading edge sensor and the speed at which beam 440 is being moved, adhesive detector 302 may be configured to scan the surfaces of fingers 408 only when adhesive is expected to be present on the surfaces of fingers 408. A microprocessor or any other suitable device, e.g., a computer system, may be used to enable adhesive detector 302 to scan the surfaces of fingers 408 only in locations of fingers 408 where an adhesive coating 418 is expected.

Like the overall dimensions of beam 404, the length L of a finger, as for example finger 408a, may also be widely varied. Emitters 308 do not typically illuminate the entire length L of the top surfaces of fingers 408. Rather, only portions of the top surfaces are illuminated, as illuminating the entire length L of the top surfaces is typically impractical, given the general configuration of fingers 408. In one embodiment, approximately twenty-five percent of the length L of the surface of a finger, e.g., finger 408a, is illuminated by an emitter, e.g., emitter 308a. It should be appreciated that the twenty-five percent of the length L of fingers 408 which is illuminated is the twenty-five percent which is closest to tips 412 of fingers 408. It is possible that in some embodiments, larger portions of fingers 408 may be illuminated.

As previously mentioned, emitters 308, as well as receivers 314, are mounted at an angle with respect to beam 404, as best shown in FIG. 4b. By angling emitters 308 with respect to beam 404 and, hence, fingers 408, a larger portion of the surfaces, e.g., approximately twenty-five percent, of fingers 408 may be illuminated. Receivers 314 are angled such that light reflected off of the surfaces of fingers 408 may be received by receivers 314. It should be appreciated that illuminating significantly more than approximately twenty-five percent of the surfaces of fingers 408 is typically difficult due to limitations imposed by the size and shape of fingers 408 and, in some cases, by the size and power of emitters, and the sensitivity of receivers.

Light emitted by emitters 308 forms a light pattern (not shown) on beam 404, or, more specifically, fingers 408, as will be described below with reference to FIGS. 5a and 5b. As emitters 308 are scanned across fingers 408, the light pattern "sweeps" across the fingers 408. When light emitted from emitters 308 comes into contact with fingers 408, the light reflects off of fingers 408 and is received by receivers 314. Receivers 314 are generally coupled to sensing circuitry (not shown) that is arranged to decipher, or otherwise interpret, the light received by receivers 314.

In the described embodiment, the light that is reflected off of a void 430, e.g., bare beam material, and light that is reflected off of adhesive coating 418 will have different properties. In other words, the intensity of light which reflects off of void 430 is different from the intensity of light which reflects off of adhesive coating 418. As such, receivers 314 and associated sensing circuitry, e.g., receiver assemblies, may be configured to determine if there is any indication that any of surfaces of fingers 408 include voids, as for example void 430. If a void is sensed, then a fault or other indicator, e.g., a counting mechanism, may be provided such that an operator is aware that a beam with an imperfect adhesive coating has been detected. As previously mentioned with respect to FIG. 2, if a void is sensed, a signal may be transmitted to a dye dispensing mechanism which is arranged to place a mark on the beam which contains the void.

Each emitter 308 and receiver 314 pair, or, more specifically, each emitter and receiver assembly pair, is arranged, in the described embodiment, to detect voids in particular associated fingers 408. By way of example, emitter 308a and receiver 314a are arranged to detect voids in the surfaces of fingers 408a and 408b. It should be appreciated that although sensing circuitry may be arranged to determine the location at which a void has occurred, the sensing circuitry is generally arranged only to identify fingers 408 on which the detected void may be present.

Figure 5A:
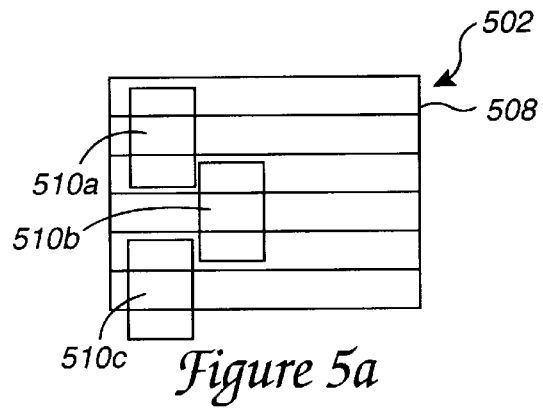
FIG. 5a is a diagrammatic representation of a light pattern generated on a beam by an adhesive detector, i.e., adhesive detector 302 of FIG. 3, in accordance with the first embodiment of the present invention.
Figure 5B:
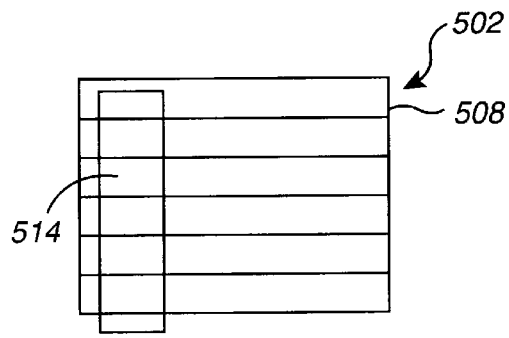
FIG. 5b is a diagrammatic representation of a composite light pattern generated on a block in accordance with the first embodiment of the present invention.

FIG. 5a is a diagrammatic representation of a light pattern generated on a beam by an adhesive detector, i.e., adhesive detector 302 of FIG. 3, in accordance with an embodiment of the present invention. A light pattern 510 is generated on a front section of a beam 502 by emitters included in an adhesive detector. Lines 508 represent the tips of fingers of beam 502. It should be appreciated that beam 502 and light pattern 510 are intended as representations of an actual beam and light pattern. Hence, details of beam 502 and light pattern 510 have been simplified purely for ease of illustration.

Section 510a of light pattern 510 is generated by emitter 308a of adhesive detector 302, which was described above with respect to FIGS. 3, 4a, and 4b. Similarly, section 510b of light pattern 510 is generated by emitter 308b of adhesive detector 302, and section 510c of light pattern 510 is generated by emitter 308c of adhesive detector 302. It should be appreciated that light pattern 510, in some embodiments, may be oblong without corners, e.g., rectangular with substantially rounded ends. The dimensions of each section 510a, 510b, 510c of light pattern 510 is dependent upon both the size and intensity of the emitters used to generate light pattern 510, as well as the relative distance between the emitters and beam 502. In the described embodiment, light pattern 510 also illuminates approximately twenty-five percent of the length of the top surface of each finger 508.

Sections 510a, 510b, and 510b are offset, as the emitters in the adhesive detector are typically also offset. As such, in order for equivalent sections of each finger 508 to be scanned, circuitry, e.g., a micro-processor circuit, coupled to the adhesive detector is preferably calibrated to scan at different, overlapping intervals. In the described embodiment, the emitter, e.g., emitter 308b of adhesive detector 302 as described above, which creates section 510b of light pattern may be arranged to begin scanning earlier than other emitters, e.g., emitters 308a and 308c, and to terminate scanning earlier than those other emitters.

A delay may be implemented in circuitry associated with the adhesive detector such that even with the offsets in emitters, the overall light pattern analyzed by the circuitry may appear to be a continuous pattern. In other words, delays may be used to enable a composite beam pattern which reflects a continuous scanning area to be analyzed. One embodiment of such a composite beam pattern is shown in FIG. 5b. Beam 502 is illuminated by a composite, continuous beam pattern 514 which is, typically, created by delaying emitter and receiver pairs as appropriate.

In general, the user interface associated with an end-jointed beam assembly line, as for example the end-jointed beam assembly line discussed above with reference to FIG. 2, may take any suitable form. By way of example, a control panel may be provided such that an operator may readily monitor the assembly line to determine the number of defective work pieces, or component beams, which have been created. One such control panel will be described with respect to FIG. 6.

Figure 6:
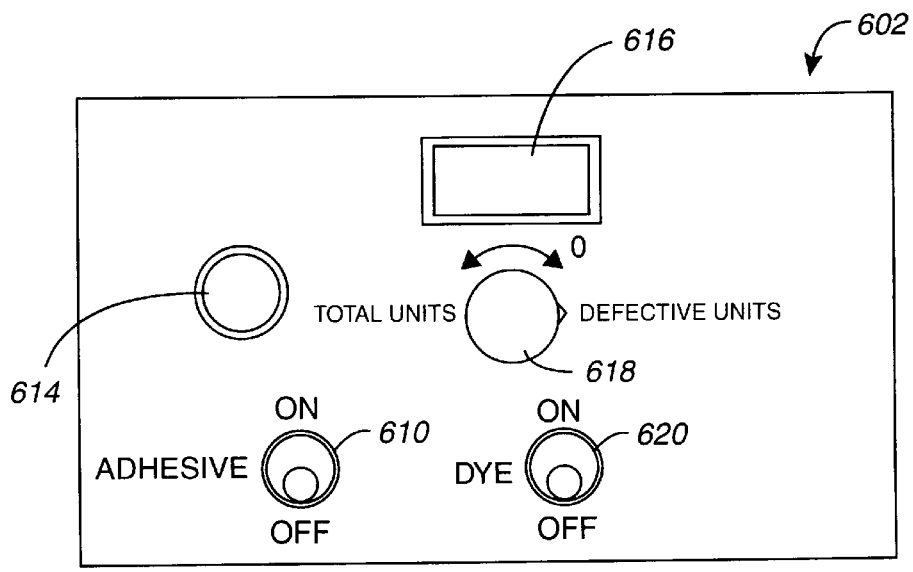
FIG. 6 is a diagrammatic representation of the panel of a control unit for an end-jointed block assembly line in accordance with the first embodiment of the present invention.

FIG. 6 is a diagrammatic representation of a panel of a control unit for an end-jointed beam assembly line in accordance with an embodiment of the present invention. It should be appreciated that, in general, panel 602 may include any number of controls and features. As shown, panel 602 includes an "adhesive on/off" control mechanism 610 which may be used to activate and to deactivate an adhesive applicator. Specifically, adhesive on/off control mechanism 610 is coupled to circuitry that may be used to control an adhesive applicator, as for example the adhesive applicator head described above with respect to FIG. 2. Although adhesive on/off control mechanism 610 may take any suitable form, in one embodiment, adhesive on/off control mechanism 610 is a toggle switch.

A warning light 614 is coupled to sensor circuitry such that when a finger-jointed beam that has a defective adhesive coating is detected, warning light 614 is illuminated to alert an operator. As will be appreciated by those skilled in the art, alternative means may also be used to physically mark a block or remove a block from a production line. A display 616, which is typically a digital display, is arranged to display any information which an operator may wish to monitor. By way of example, display 616 may display the number of total finger-jointed beams which have been coated with adhesive. Alternatively, display 616 may display the number of defective units which have been detected. It should be appreciated that display 616 may generally be arranged to display other information which is available within an adhesive application and detection system. Such information may include, but is not limited to, the amount of time the adhesive application and detection system has been on-line, or the number of defective finger-jointed beams, or blocks, which have been detected over a fixed period of time.

An option control mechanism 618 is arranged such that different display options may be selected. That is, option control mechanism 618 is coupled to display 616 such that whichever option is selected for display using option control mechanism 618 is then displayed on display 616. As shown, option control mechanism 618 is an incremental switch which may be switched between different options, e.g., an option to display the number of defective finger-jointed beams and an option to display the number of total finger-jointed beams which have been coated with adhesive.

A dye control mechanism 620 is coupled to circuitry which may be used to activate and deactivate the dye mechanism or, more generally, the indicator mechanism which was described earlier with respect to FIG. 2. As shown, dye control mechanism 620 is a toggle switch, although dye control mechanism 620 may take on any number of suitable forms. When it is not desirable for a finger-jointed beam to be marked with dye, dye control mechanism 620 may be used to deactivate the dye mechanism. In the described embodiment, dye control mechanism 620 is coupled to a valve (not shown) which actuates the dye control mechanism.

Panel 602 may include any number of additional controls and features, as mentioned above. By way of example, various reset buttons may be included as a part of panel 602 such that different counters may readily be reset. In addition, in one embodiment, as the adhesive application and detection systems may be arranged to automatically shut down in the event that a predetermined number of defective finger-jointed beams has been detected, panel 602 may also include indicators which alert a user that systems have been shut down. It should be appreciated that such indicators may generally be audio or visual.

As previously mentioned, processes used to apply and to detect adhesive may vary. One embodiment of an adhesive application and detection system, as described above, involves using principles of reflectivity for detecting imperfections in adhesive coatings. Another embodiment of an adhesive application and detection system involves using principles of luminescence to detect imperfections in adhesive coatings. Luminescence is associated with light emitted by sources other than hot incandescent bodies. Hence, changes in luminescence on a surface allow imperfections to be identified, as the luminescence of a coated surface is generally higher than the luminescence associated with an uncoated surface which defines a void.

Figure 7:
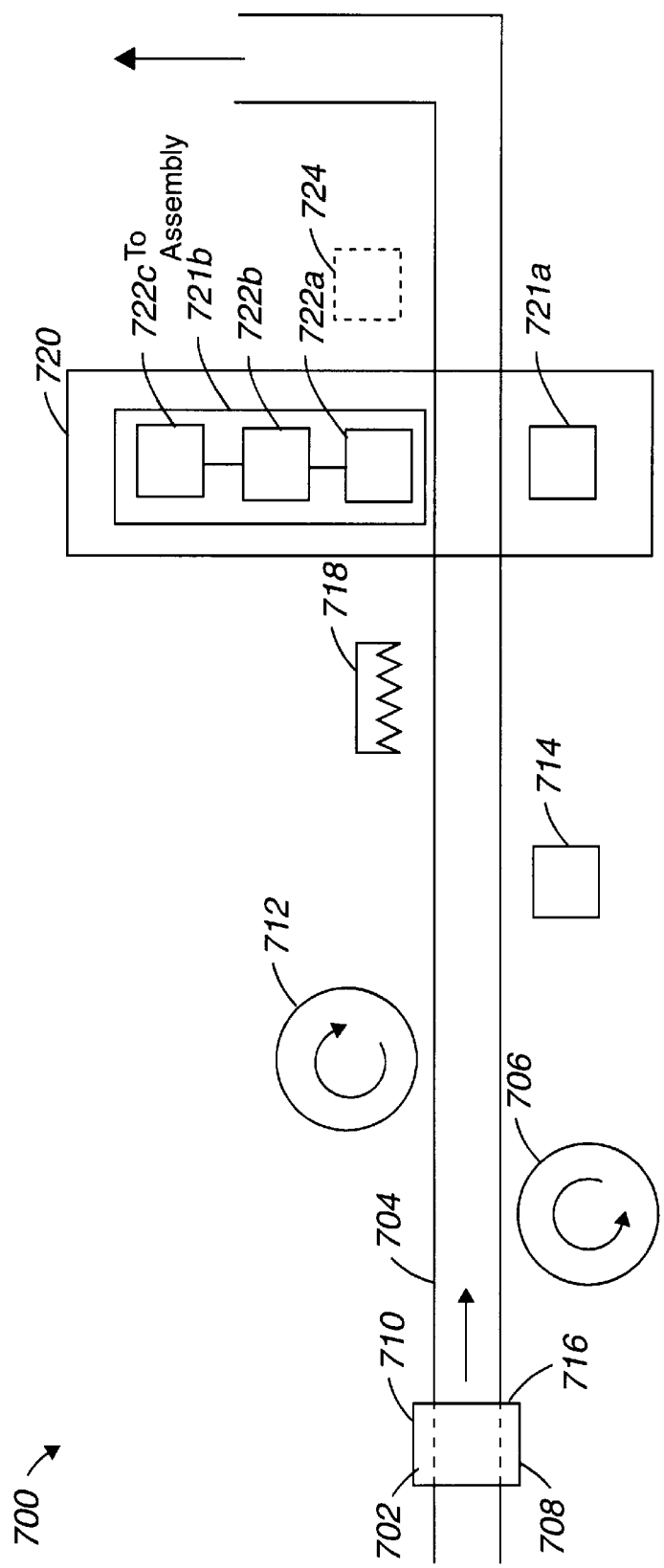
FIG. 7 is a diagrammatic representation of a portion of the fabrication process of an end-jointed block in accordance with a second embodiment of the present invention.

Referring next to FIG. 7, a process of applying and detecting adhesive using principles of luminescence will be described in accordance with a second embodiment of the present invention. A work piece 702, e.g., a beam or a block of wood, associated with an assembly line 700 is oriented on a conveyer belt or chain 704 which is generally arranged to transport work piece 702 between different processes along assembly line 700. Although work piece 700 may be transported using substantially any conveyer belt 704, in the described embodiment, conveyer belt 704 includes lugs on which work piece 700 may be situated.

In the described embodiment, work piece 700 is arranged to be formed into a part of an overall finger jointed beam. It should be appreciated, however, that in alternate embodiments, work piece 700 may be an I-joist, or part of an overall edge-glued board. A first cutter head 706 is arranged to profile work piece 702 such that fingers (not shown) are formed in a first end 708 of work piece 702. Fingers which are cut into work piece 702 at first end 708 are typically arranged to be interlocked with fingers of another work piece. The number of fingers cut into work piece 702 at first end 708 may range from approximately two fingers to approximately sixty fingers. In general, first cutter head 706 may generally be any type of cutting mechanism, as for example a circular saw cutting mechanism or a stacked knife assembly. When fingers are desired in both first end 708 and a second end 710 of work piece 702, a second cutter head 712 is arranged to profile fingers in second end 710.

Once fingers are profiled in work piece 702, conveyer belt 704 transports work piece 702 into a sensing range of a block sensor 714. Block sensor 714 is generally arranged to detect the presence of work piece 702 on a lug of conveyer belt 704, and may be located on either side of conveyer belt 704, and even over or under conveyer belt 704. Block sensor 714 may include a rotary encoder attached to a drive shaft of conveyer belt 704 such that work piece 702 may be located. Alternatively, block sensor 714 may be either a leading edge block sensor, which is arranged to sense when a leading edge 716 of work piece 702 passes through its sensing range, or a trailing edge block sensor, which is arranged to sense when a trailing edge of work piece 702 passes through its sensing range. One suitable leading edge block sensor was described above with respect to FIG. 2.

After work piece 702 passes through the sensing range of block sensor 714, a coating such as an adhesive coating may be applied using an applicator head 718. Although any suitable applicator head 718 may be used in the application of adhesive to the surfaces of fingers of work piece 702, applicator head 718 is preferably either the applicator head described in above-mentioned U.S. Pat. No. 3,938,367, or in U.S. Pat. No. 4,220,114. It should be appreciated that for an embodiment in which work piece 702 has no fingers, an applicator head 718 that is suitable for such a work piece may be used. As shown, applicator head 718 is arranged to dispense adhesive only on fingers profiled in second end 710 of work piece 702. An additional applicator head (not shown) may be added to assembly line 700 to serve the purpose of coating first end 708 of work piece 702 with adhesive.

Once adhesive is applied to work piece 702, conveyer belt 704 transports work piece 702 to a detector mechanism 720. In the described embodiment, detector mechanism 720 is generally arranged to sense whether adhesive has been properly applied to the fingers of work piece 702. By way of example, if there is an imperfection such as a void in the adhesive coating on a finger of work piece 702, detector mechanism 720 will detect the void and alert an individual who is monitoring end-jointed beam assembly line 700 that the adhesive coating on work piece 702 is defective.

Detector mechanism 720 includes a frame sensing unit 721*a* and an adhesive detection unit 721*b*. Frame sensing unit 721*a* is arranged to locate work piece 702 such that the edges of work piece 702 may be identified for adhesive detection unit 721*b*. Adhesive detection unit 721*b* includes a luminescence sensor 722*a* which is arranged to measure the luminescence associated with a coated surface of work piece 702. Luminescence sensor 722*a* is generally arranged with an objective lens that may be arranged, based upon its focal point, to alter the sensing distances associated with luminescence sensor 722*a*. Although any suitable luminescence sensor 722*a* may generally be used, one particularly suitable luminescence sensor is the LUT-15 luminescence sensor, available commercially from Sick Optic-Electronic of Germany.

Figure 8:
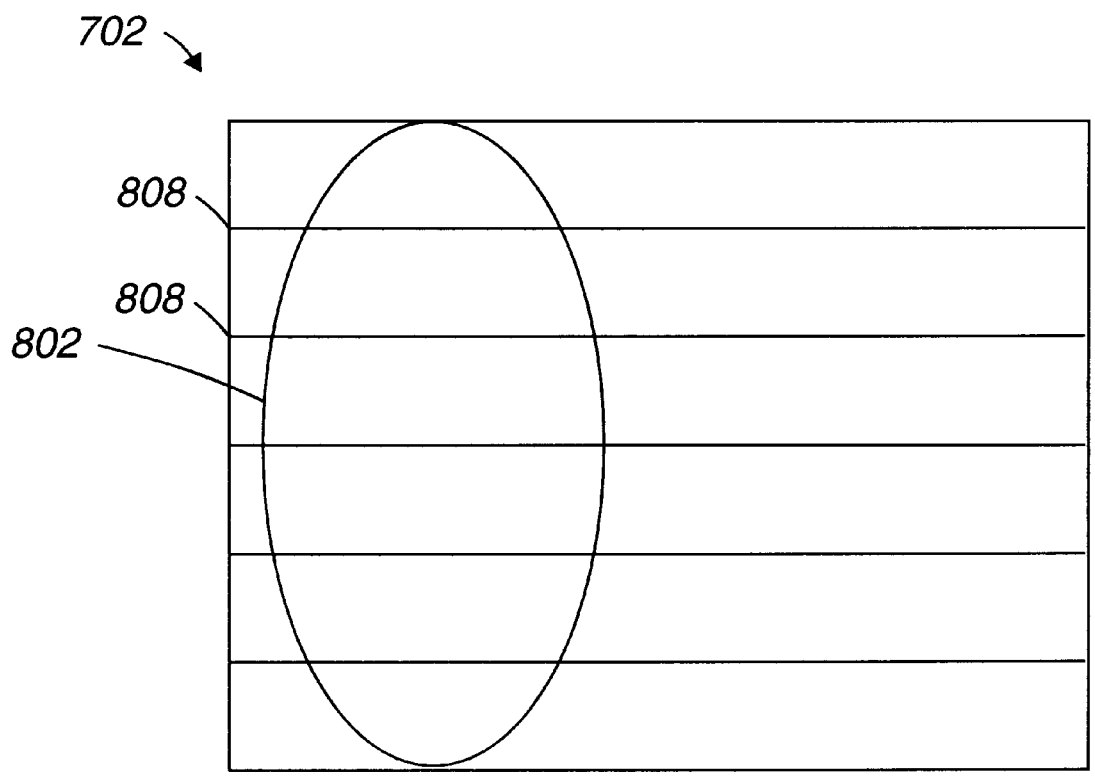
FIG. 8 is a diagrammatic representation of a light pattern generated on a beam by a luminescence adhesive detector, i.e., adhesive detector 702 of FIG. 7, in accordance with the second embodiment of the present invention.

The sensing pattern "projected" onto work piece 702 by luminescence sensor 722*a* may vary depending upon the particular configuration of the luminescence sensor, e.g., an objective lens associated with luminescence sensor may vary. In the described embodiment, the sensing pattern may be either elliptical or circular, although the sensing pattern may also be substantially rectangular. Referring to FIG. 8, an elliptical sensing pattern 802 is shown as being "projected" onto work piece 702 or, more specifically, fingers 808 of work piece 702.

Returning to FIG. 7, luminescence sensor 722*a* is coupled to an analog to digital (A/D) convertor which converts analog luminescence signals into digital signals which may be used by a programmable logic controller (PLC) 722*b* to determine when an imperfection in a coated surface of work piece 702 is present. In general, digital signals associated with an imperfection such as a void are lower than digital signals associated with a properly coated portion of the surface. That is, the luminescence of a coated surface is generally higher than the luminescence of an uncoated surface. As such, PLC 722*b* is typically arranged to identify when digital signals below a predetermined threshold are received. When digital signals below the predetermined threshold are associated with work piece 702, work piece 702 may be identified as including an imperfection. In one embodiment, when any digital signals are below the predetermined threshold during the course of sensing work piece 702, work piece 702 is considered to include an imperfection. Alternatively, in other embodiments, a percentage of digital signals associated with work piece 702 that fall below the predetermined threshold may be met before work piece 702 is considered to include an imperfection. It should be appreciated that the predetermined threshold may be selected to reflect the requirements of a particular application.

PLC 722*b* is typically coupled to an interface panel 722*c*. While interface panel 722*c* may include any number of features, in the described embodiment, interface panel 722*c* may include a screen, or multiple screens, which displays a block count, glue-on delay, glue-off delay, an adhesive flush switch, an adhesive threshold setting, and a time delay setting for indicating mechanism 724. The block count generally indicates the total number of work pieces that have passed through the board edge sensor. The glue-on delay indicates the amount of time it nominally takes for the leading edge of work piece 702 to travel between the board edge sensor and applicator 718, while the glue-off delay indicates the amount of time it takes for the trailing edge of work piece 702 to travel between the board edge sensor and application 718. In general, the adhesive flush switch enables an operator to flush or prime the overall system with adhesive, or flush the adhesive system with a cleaning agent by, for example, manually or automatically opening an adhesive valve. The adhesive threshold setting enables the operator to set a threshold numerical value which is arranged to activate indicating mechanism 724 when an analog signal that has been converted to a digital signal drops below the threshold numerical value. The time delay setting for indicating mechanism 724 typically allows an operator to set a time delay, when desired, in order to prevent indicating mechanism 724 from triggering until work piece 702 has traveled from adhesive detection sensor 721b to underneath, or in front of, indicating mechanism 724. It should be appreciated that not all indicating mechanism 724 will utilize a time delay setting.

A failed unit indicating mechanism 724, as shown, may be located such that work piece 702 passes from detector mechanism 720 to indicating mechanism 724. In one embodiment, indicating mechanism 724 is a dye dispensing mechanism that is arranged to place a dye mark on work piece 702 in the event that there is a defect in the adhesive coating on work piece 702. Indicating mechanism 724 is generally coupled to detector mechanism 720, since the operation of indicating mechanism 724 is dependent upon whether a defect has been detected by adhesive detector 720. In some embodiments, indicating mechanism 724 may be an air kicker that is arranged to "kick" or otherwise remove imperfect work pieces from assembly line 700. Alternatively, indicating mechanism 724 may be a light that turns on, or a horn that sounds, when an imperfect work piece is identified.

In the described embodiment, if work piece 702 is defective, work piece 702 may be removed from assembly line 700. Alternatively, if work piece 702 is not defective and, therefore, is not marked, conveyer belt 704 moves work piece 702 from the adhesive application and detection portion of assembly line 700 to an assembly portion of assembly line 200 that is arranged to assemble work pieces together. Assembling work pieces together generally involves bonding work pieces together to create an overall beam or board, e.g., interlocking and joining complementary ends of work pieces, as will be appreciated by those skilled in the art.

Although only a few embodiments of the present invention have been described, it should be understood that the present invention may be embodied in many other specific forms without departing from the spirit or scope of the invention. By way of example, although the detector mechanism has been described in terms of an adhesive detector mechanism, the detector mechanism may also be used in conjunction with a process of laminating beams without departing from the spirit or the scope of the present invention. In other words, voids or other imperfections in coatings of laminating material may also be detected using the detector mechanism. Further, voids or other imperfections in other coatings, as for example a coating of paint, may also be detected using the detector mechanism.

In addition, although the detector mechanism utilizes principles of either reflectivity or luminescence to locate imperfections in an adhesive coating, it should be appreciated that the detector mechanism may utilize any suitable principle to determine whether imperfections exist in the adhesive coating. By way of example, the detector mechanism may be a vision system, or be a system that is arranged to sense the differences in thickness of a bare finger and a finger with an adhesive coating. The detector mechanism may also make use of ultrasonic principles to detect the differences between a bare portion of a finger and a portion of a finger that is covered with a layer of adhesive. In some embodiments, the detector mechanism may be arranged to sense color variations between bare and coated portions of a finger.

While the detector mechanism has been described as being used to locate voids in adhesive coatings on the top or bottom surfaces of fingers, the detector mechanism may varied to facilitate the location of voids in adhesive coatings on both the top and bottom surfaces of fingers. For example, the above-described detector mechanism may be rotated by 90 degrees such that the detector mechanism is more appropriately oriented to scan the bottom surfaces of fingers. In one embodiment, in order to scan both the top surfaces and the bottom surfaces of fingers to be scanned, an end-jointed beam assembly line may be modified to include both a "top sensing" detector mechanism and a "bottom sensing" detector mechanism without departing from the spirit or the scope of the present invention. Alternatively, a finger-jointed wood piece may be flipped such that the top and bottom surfaces of the fingers may both be scanned by a single detector mechanism.

The process of detecting adhesive on the fingers of a block has been described in terms of scanning the beam in a direction that is parallel to the fingers. However, it should be appreciated that the process of detecting adhesive on fingers may also be performed by scanning the fingers in a direction that is perpendicular to the fingers without departing from the spirit or the scope of the present invention. In other words, each emitter and receiver pair, rather than being arranged to scan only particular fingers, may instead be arranged to scan a particular portion of each finger joint.

It should be appreciated that the detector mechanism may be modified to detect any imperfections in an adhesive coating, as well as a coating of laminating material or any suitable material, on any number of different surfaces. In other words, the detector mechanism may be altered for use with boards which do not include fingers. By way of example, the sensors in the detector mechanism may be reoriented to enable the detector mechanism to sense imperfections in an adhesive coating formed on a flat surface of a "regular," e.g., non-jointed edge-glued, beam, or an I-joice beam. Further, such imperfections are not limited to voids. For example, the imperfections may include unwanted residue that is present in adhesive coatings.

While a PLC has been described as being suitable for use as a part of a detector mechanism that operates using principles of luminescence, it should be appreciated that in lieu of a PLC, other devices may be used to either read and/or process luminescence data. For instance, dedicated circuitry or, in some cases, a computer system may be implemented for such a purpose. Therefore, the present examples are to be considered as illustrative and not restrictive, and the invention is not to be limited to the details given herein, but may be modified within the scope of the appended claims.

What is claimed is:

1. A method for preparing a first work piece to facilitate joining the first work piece to a second work piece using a finger joint, the method comprising:

forming at least one finger on a first end of the first work piece;

applying a coating to the finger of the first work piece;

checking the coating applied to the finger of the first work piece to determine whether the coating includes an imperfection before the first work piece is joined to the second work piece using a sensing mechanism arranged to scan across at least a portion of the finger, wherein checking the coating includes obtaining luminescence data by scanning across the portion of the finger, the sensing mechanism being arranged to substantially reduce the luminescence data; and identifying the first work piece as including an imperfection when it is determined that the coating includes the imperfection.

2. A method for preparing a first work piece as recited in claim 1 wherein the coating is an adhesive coating, and when it is determined that the coating does not include an imperfection, the first work piece is joined to the second work piece.

3. A method for preparing a first work piece as recited in claim 1 wherein checking the coating to determine whether the coating includes the imperfection includes determining whether the coating defines a void.

4. A method for preparing a first work piece as recited in claim 1 wherein checking the coating to determine whether the adhesive coating includes the imperfection further includes:

substantially covering at least a section of the portion of the finger with signals emitted using the sensing mechanism, wherein at least some of the emitted signals are substantially reflected off of the finger; and receiving the reflected signals within the sensing mechanism, wherein the magnitude of the received reflected signals are used to determine whether the coating includes the imperfection.

5. A method for preparing a first work piece as recited in claim 4 wherein the received reflected signals are analog signals, the method further including:

converting the analog signals to digital signals; and using the digital signals to determine whether the coating defines the imperfection.

6. A method for preparing a first work piece as recited in claim 1 wherein:

a plurality of fingers are formed on the first work piece;

an adhesive coating is applied to each of the fingers; and each of the fingers is checked for imperfections.

7. A method for preparing a first work piece to facilitate joining the first work piece to a second work piece using a finger joint, the method comprising:

forming at least one finger on a first end of the first work piece;

applying an adhesive coating to the finger of the first work piece; and checking the adhesive coating applied to the finger of the first work piece to determine whether the adhesive coating includes an imperfection using a sensing mechanism arranged to scan across at least a portion of the finger, wherein when it is determined that the adhesive coating includes the imperfection, the first work piece is identified as including an imperfection; and marking the first work piece to indicate that the first work piece includes the imperfection when it is determined that the adhesive coating includes the imperfection.

8. A method for preparing a first work piece as recited in claim 7 wherein marking the first work piece includes marking the first work piece with dye.

9. A method for determining whether a coating has been properly applied to a surface of a work piece, the method comprising:

scanning a portion of the surface of the finger using a sensing device, the sensing device being arranged to substantially gather luminescence information from the portion of the surface of the finger, the sensing device including a first assembly arranged to emit signals and a receiver assembly arranged to receive the luminescence information; and determining whether the coating defines an imperfection, wherein when the coating does not define an imperfection, the coating is determined to be properly applied.

10. A method for determining whether a coating has been properly applied as recited in claim 9 farther including:

identifying the work piece as including the imperfection when it is determined that the coating does define the imperfection.

11. A method for determining whether a adhesive coating has been properly applied as recited in claim 10 wherein identifying the work piece as including the imperfection includes one of physically marking the work piece, providing an audible signal, and providing a visible signal.

12. A method for determining whether a coating has been properly applied as recited in claim 9 wherein determining whether the coating defines the imperfection includes determining whether luminescence information received by the receivers are within a particular range of magnitudes, the particular range of magnitudes being arranged to indicate whether the imperfection is present.

13. An apparatus for detecting an imperfection in an adhesive coating formed on a finger of a first work piece to be coupled to a second work piece using a finger joint, the apparatus comprising;

a sensing assembly arranged receive luminescence signals substantially reflected off of the finger; and a control assembly arranged to determine whether the adhesive coating on the finger includes an imperfection when the first work piece is not yet coupled to the second work piece based at least in part upon the magnitude of the luminescence signals received by the analog sensing assembly.

14. An apparatus for detecting an imperfection in an adhesive coating as recited in claim 13 wherein the sensing assembly includes an emitter for directing signals at the finger and a receiver for collecting reflected signals.

15. An apparatus for detecting an imperfection in an adhesive coating as recited in claim 13 wherein the sensing assembly is an analog sensing assembly, and the control assembly includes an analog to digital converter.

16. A method for preparing a first work piece to facilitate joining the first work piece to a second work piece using a finger joint, the method comprising:

forming at least one finger on a first end of the first work piece;

applying an adhesive coating to the finger of the first work piece; and checking the adhesive coating applied to the finger of the first work piece to determine whether the adhesive coating includes an imperfection before the first work piece is joined to the second work piece by the finger of the first work piece using a sensing mechanism arranged to scan across at least a portion of the finger, the sensing mechanism including an emitter device and a receiver device, wherein when it is determined that the adhesive coating includes the imperfection, the first work piece is identified as including an imperfection.

17. A method for determining whether an adhesive coating has been properly applied to a finger of a finger-jointed work piece, the method comprising:

scanning a portion of the surface of the finger using a sensing device, the sensing device including an emitter assembly arranged to emit light waves and a receiver assembly arranged to receive light waves; and determining whether the adhesive coating defines a void in the portion, wherein when the adhesive coating does not define a void in the portion, the adhesive coating is determined to be properly applied.

18. A method for preparing a first work piece to facilitate joining the first work piece to a second work piece, the method comprising:

forming at least one joinable surface on a first end of the first work piece;

applying a coating to the joinable surface of the first work piece;

checking the coating applied to the joinable surface of the first work piece to determine whether the coating includes an imperfection before the first work piece is joined to the second work piece using a sensing mechanism arranged to scan across at least a portion of the joinable surface to gather luminescence data, the sensing mechanism being arranged to gather and to analyze luminescence data, wherein when it is determined that the coating includes the imperfection, the first work piece is identified as including an imperfection; and joining the first work piece to the second work piece when it is determined that the coating does not include the imperfection.

19. A method for determining whether a coating has been properly applied as recited in claim 9 wherein the luminescence information includes absolute measurements, and wherein determining whether the coating defines an imperfection includes comparing the absolute measurements against a threshold value, wherein when at least a portion of the absolute measurements has a value that is less than the threshold value, the coating defines the imperfection.

20. An apparatus for detecting an imperfection according to claim 13 wherein the sensing assembly includes a luminescence sensor, the luminescence sensor including an objective lens that is arranged to alter a sensing distance between the sensing assembly and the finger.

* * * * *